US006479461B1

(12) United States Patent
Bousquet et al.

(10) Patent No.: US 6,479,461 B1
(45) Date of Patent: Nov. 12, 2002

(54) USE OF ALKYLMONOGLUCOSIDES AS MOLECULAR VECTORS

(75) Inventors: Marie Pierre Bousquet, Toulouse (FR); Rene-Marc Willemont, Pompertuzat (FR); Pierre Monsan, Mondonville (FR); Emmanuel Boures, Clermont-Ferrand (FR); Arnaud Messager, Riom (FR)

(73) Assignee: Ulice, Riom (FR)

( * ) Notice: Subject to any disclaimer, the term of this patent is extended or adjusted under 35 U.S.C. 154(b) by 0 days.

(21) Appl. No.: 09/509,078

(22) PCT Filed: Sep. 22, 1998

(86) PCT No.: PCT/FR98/02028

§ 371 (c)(1),
(2), (4) Date: Jun. 14, 2000

(87) PCT Pub. No.: WO99/15147

PCT Pub. Date: Apr. 1, 1999

(30) Foreign Application Priority Data

Sep. 22, 1997 (FR) .............................................. 97 11766

(51) Int. Cl.⁷ ..................... A61K 31/7024; C07H 15/04
(52) U.S. Cl. .......................... 514/25; 536/4.1; 536/124; 435/74
(58) Field of Search ..................... 536/4.1, 124; 514/25; 435/74

(56) References Cited

U.S. PATENT DOCUMENTS

| | | | | |
|---|---|---|---|---|
| 4,565,863 A | * | 1/1986 | Bollag et al. ............... | 536/18.2 |
| 4,608,370 A | * | 8/1986 | Aronsohn .................... | 514/159 |
| 4,959,459 A | * | 9/1990 | David et al. ................. | 536/1.1 |
| 5,478,560 A | * | 12/1995 | Tominaga et al. ........... | 424/401 |
| 5,773,256 A | * | 6/1998 | Pelenc et al. ............... | 435/74 |
| 5,814,662 A | * | 9/1998 | Znaiden et al. ............. | 514/557 |

FOREIGN PATENT DOCUMENTS

| | | |
|---|---|---|
| JP | 63-218631 | 9/1988 |
| JP | 5-043428 | 2/1993 |
| JP | 9-268194 | * 10/1997 |
| JP | 9-278788 | * 10/1997 |
| WO | WO 95/14705 | 6/1995 |

OTHER PUBLICATIONS

Caplus abstract of JP 9–278788, 1997.* de Goede, A. et al "Selective lipase–catalyzed esterification of alkyl glycosides" Biocatalysis, vol. 9, pp. 145–155, 1994.*

*Chemical Abstracts* 126:176810, T. Halmos, "Synthesis of Glucose–chlorambucil Derivatives and Their Recognition By the Human GLUT1 Glucose Transporter", *Eur. J. Pharmacol.* (1996) vol. 318, No. 2/3, pp 477–484.

* cited by examiner

*Primary Examiner*—James O. Wilson
*Assistant Examiner*—Leigh C. Maier
(74) *Attorney, Agent, or Firm*—Young & Thompson

(57) ABSTRACT

The invention concerns the use as molecular vector in pharmaceutical, cosmetic and food products of alkylmonoglucosides of general formula (I) in which $R_1$ is a linear or branched $C_2-C_{18}$ alkyl radical.

1 Claim, No Drawings

USE OF ALKYLMONOGLUCOSIDES AS MOLECULAR VECTORS

The present invention concerns the use of alkylmonoglucosides and more particularly n-butyl-α-D-monoglucopyranose, named hereafter α-butylglucoside as molecular vector, and the preparation of new compounds obtained by grafting α-butylglucoside onto certain compounds and their uses.

We have noted that a need existed to modify numerous cosmetic or pharmaceutical active ingredients and/or food ingredients in order to improve:
- their bioavailability
- their toxicity
- their liposolubility
- their hydrosolubility The present invention proposes to respond to these needs. It concerns the use, in pharmaceutical, dermatological, cosmetic or food domains, of alkylmonoglucosides as transcutaneous or transmucous membrane molecular vectors having the general formula:

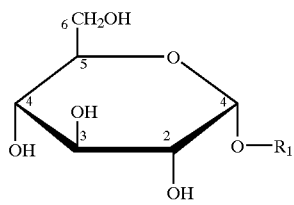

in which $R_1$ is a $C_2$ to $C_{18}$ alkyl, linear or branched radical. By "molecular vector" a compound is meant, which after chemical reaction with an active compound gives a vectorized active compound which penetrates the skin or a mucous membrane more easily than the initial active compound.

The invention also concerns the use, in a pharmaceutical, dermatological, cosmetic or food composition, of vectorized active ingredients with the general formula:

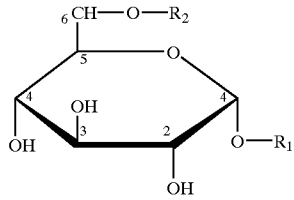

where $R_2$ is a —CO—R group where R is a hydrocarbonated, linear, branched, saturated or unsaturated ethylene radical; a group derived from retinol (vitamin A) or from one of its derivatives, notably retinoic acid, ascorbic acid (vitamin C) or one of its derivatives, of a tocopherol amongst which are vitamin E and the D vitamins; a group derived from polyphenols, for example a residue of polyhydroxylated derivatives of flavan; or a radical

where X is an aliphatic chain which is functionalized or not.

In these vectorized active ingredients, the active molecule is linked by covalence to position 6 of the vector. The invention stems from the fact that we have reduced the toxicity of exfoliant agents used in cosmetics and/or dermatology by grafting onto α-butylglucoside.

Cosmetic and/or dermatological compositions have, amongst others, a vocation of acting on the protection function of the skin which necessitates the direct influence of the condition of the corneal layer. It is known that if this corneal layer contains too many dead cells, it doesn't protect any more. It must then be removed to allow another layer of cells to maintain an efficient barrier against external aggressions, and the cosmetic and dermatological active ingredients to penetrate it. Such is the known and allotted role of Alpha Hydroxy Acids or AHA.

The AHA are organic acids with an alcohol function on the neighbouring carbon of the one (in alpha position) carrying the carboxylic acid function. We group together more particularly glycolic acid, lactic acid, malic acid, tartaric acid, citric acid, gluconic acid as well as certain analogues of AHA like salicylic acid and serine in this family of compounds.

These AHA have recognised and measurable efficacy but they also present some drawbacks. These AHA are often irritants and have a poor bioavailability: they sometimes penetrate too rapidly into the deep layers of the skin. In Parfums Cosmétiques Arômes 122,66–72 (April, May 1995) improvements proposed by the suppliers of raw cosmetic materials are described to make these compounds less irritant and to slow down their penetration into the skin.

A proposed improvement attempt consists of encapsulating these AHA in capsules in order to slow down the diffusion of AHA. Unfortunately, it is difficult to know with exactitude the percentage of active ingredients encapsulated and even more difficult to evaluate the percentage of active ingredients liberated into the skin.

Another attempt consists of lipophilising these AHA by grafting a lipophile compound (fatty alcohol, alkyl chains) by esterification. However, the action of these compounds is reduced because of their lipophile nature. In fact, they diffuse only with great difficulty into the stratum corneum into which they are stopped by the presence of aqueous compartments in the intercorneocytory spaces.

We have expanded this reflection to saturated and unsaturated fatty acids. In fact, the corneal layer is made up of a compact mass of 20 layers of inactive cells, embedded in a system of double lamellar layers of lipids. This structure of the stratum corneum as well as the lipophile nature of the lipid barrier protects the skin against the drying out provoked by the imperceptible loss of transepidermal water. Cosmetic and/or dermatological compositions have, amongst others, a vocation of acting on the protection function of the skin and to improve the appearance. If the intercellular lipids of the corneal layer are altered, the skin no longer protects.

Unsaturated fatty acids, such as linoleic acid, are an important factor for the construction and repair of the lipid barrier. They function as precursor molecules for the synthesis of a signal substance which controls the proliferation and the activity of the cells.

In addition, unsaturated fatty acids also directly take part in the regulation of the cutaneous permeability. These are non occlusive lipophile substances capable of making a more or less continuous film at the cutaneous surface but above all likely to incorporate themselves in the intercellular cement thus playing an active role in the regulation of hydration. Their biological activity is regulated by the position of the double link closest to the terminal methyl group.

The clinically observed cases of cutaneous alteration like acne show that a sufficient supply of unsaturated fatty acids in the skin is necessary to maintain the functioning of the lipid barrier.

Unsaturated fatty acids thus have an essential role in the physiology of the skin. Their topical administration however poses problems, problems that we propose to resolve by vectoring them.

The action of these compounds are reduced as they only diffuse with difficulty into the stratum corneum: they are stopped by the presence of aqueous compartments contained in the intercorneocytary spaces. The grafting of these acids onto α-butylglucoside increases the hydrophile nature and thus optimises the penetration of these active ingredients into the epidermis.

In addition, the penetration of these compositions into the epidermis poses a problem because of their lipophile nature. Their introduction into emulsions stabilised by a monolayer of tensioactives practically does not improve this state of fact given that these emulsions break as soon as they are applied onto the skin. An oily phase containing the unsaturated fatty acids thus rests on the surface of the skin. Thanks to the invention the increase of the hydrophilic nature by the hydroxyl functions free from the glucose part improves penetration and allows an optimised usage of unsaturated fatty acids in water in oil or oil in water emulsions.

By extension, this principle can be applied to numerous active lipophile compounds with a physiological action on the skin. As an example, we can cite the esterifiable derivatives of the lipophile vitamins A,D,E or F, essential oils, solar filters, anti-inflammatories as well as bio-stimulant agents of lipids and/or protein syntheses. The document FR-A-94 12005 exposes different solutions consisting of preparing oil emulsions in specific water.

Certain cosmetic, dermatological pharmaceutical active ingredients and/or food ingredients are unstable as they are sensitive to exterior factors like light or heat.

Moreover, different means have been used to stabilise these compounds. One of these means lies for example in blocking the sensitive site by esterification with phosphate, sulphate, and alkyl derivatives and to employ these derivatives instead of the non-modified compound. These derivatives have a less good activity and are sometimes more toxic than the active ingredient free by the presence of phosphated, sulphated or alkyl residues.

Another means consists of blocking the site with a glycosidic derivative. A precursor of active ingredients is thus obtained which after application on the skin is stopped by the cutaneous enzymes or is hydrolysed after oral administration. The active ingredient is then liberated. Thus, the patent EP-A-627441 describes the preparation and the use of glucosylate of ascorbic acid topically, stopped by the enzymes of the skin which then liberate ascorbic acid. But the use of such derivatives also brings about the liberation of glucose at the surface of the skin which favours the development of pathogenic cutaneous flora.

The applicant has now found in an unexpected manner that certain alkylmonoglucosides and more particularly α-butylglucoside, allowed all these improvements whilst avoiding the problems described in the prior art.

The present invention thus has as its principal object the preparation and use of alkylmonglucosides and more particularly α-butylglucoside in a food, cosmetic, dermatological or pharmaceutical composition.

The alkylglucosides, more particularly α-butylglucoside, as well as certain alkylglucoside esters, can be obtained by enzymatic route as is described in the patent application PCT/FR92/00782 belonging to the applicant.

The products stemming from this process are anomerically pure (α) and are monoglucosides. Because of the quasi absence of anomer β, the compounds thus obtained, have specific physico-chemical properties, such as the point of fusion and the solubility. The amphiphile nature makes the α-butylglucoside miscible in all proportions with saturated and unsaturated acids in a melted medium and soluble in the aqueous mediums and polar organic synthesis solvents.

TABLE n°1 solubility of α-butylglucoside in water and in different solvents

| Solvent | Solubility at 20° C. % (p/p) |
|---|---|
| Water | 60 |
| Ethanol (95/96%) | 70 |
| Glycerol | 70 |
| Acetonitrile | 50 |
| Dichloromethane | 70 |
| Dioxane | 70 |
| Polyethylene glycol 200 | 70 |
| Propylene glycol | 70 |

We can modify the active ingredients and/or ingredients by α-butylglucoside to make them lipophile or hydrophilic. It thus becomes possible to modulate their physico-chemical behaviour as well as their penetration, which makes it possible to strongly reduce any risk of irritation.

The active ingredients possessing at least one acid or ester function are able to be grafted with the aid of a chemical or enzymatic catalyst, notably hydrolysed trialglycerols (E.C no. 3.1.1.3) which can act as carboxyesterase. We have used Novozym® or Lipozyme® as they are easily accessible commercial enzymes. The active ingredients to which the invention applies concerns those comprising for example:

At least one acid function and more particularly amino and α-hydroxy acids such as glycolic acid, lactic acid, malic acid, tartaric acid, citric acid, gluconic acid, salicylic acid and serine.

An acid function and notably butyric acid, saturated and unsaturated fatty acids, and more particularly oleic acid, erucic acid, ricinoleic acid, linoleic acid, and alpha and gamma linoleic acid.

At least one ester function like methyl lactate, ethyl lactate, butyl lactate or any other esterified derivative of the acids mentioned above. It can be cetone esters and notably dihydroxyacetone ester. The ester used according to the invention includes one or several ester functions with linear or branched chain, saturated or unsaturated, with from 2 to 25 atoms of carbon, possibly comprising one or several substituents.

At least one carboxylic esterifiable function, and notably, vitamin derivatives such as retinol (vitamin A) and its derivatives (notably retinoic acid), ascorbic acid (vitamin C) and its derivatives, tocopherols, amongst which are vitamin E and the D vitamins, as well as amino acids, peptides and their derivatives. It can also concern derivatives of polyphenols and more particularly polyhydroxylated derivatives of flavan and especially flavan-3-ol.

By vectorized active ingredients, we mean the coupling by a chemical covalent link of the active ingredient or ingredient to the position 6 of an alkylmonoglucoside and more particularly to α-butylglucoside, of a formula

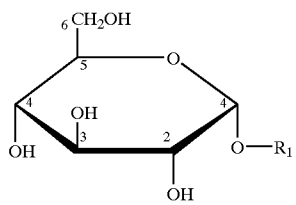

in which $R_1$ is $C_{2-18}$ alkyl, linear or branched radical, preferably a butyl radical.

The vectorized active ingredients can be used according to the invention in a quantity from 0.1 to 50% in weight, and preferably from 0.5 to 50% in weight when it concerns vectorized cetone ester and notably vectorized dihydroxyacetone ester and from 0.1 to 10% in weight where other vectorized active ingredients are concerned.

As an example, and without it being considered as limiting, the preparation of two types of derivatives is described according to the present invention.

EXAMPLE 1

Preparation of Lactic Ester of α-Butylglucoside

In a flask adaptable to a rotating evaporator, 120 g of α-butylglucoside is placed in 1 litre of butyl L-lactate at 60° C. under vacuum. 100 g of Novozym®, of the lipase of Candida antarctica immobilised on a solid support (Novo Industri, Denmark). The solution is placed again under vacuum (15 mbars) at 60° C. for at least 48 hours.

At the end of the reaction, the reaction medium is centrifuged and filtered to completely eliminate the Novozym®. The filtrate is collected for purification. The lactate of a-butylglucoside is purified by two successive extractions in hexane. The butyl lactate is extracted in the organic phase. The lactate of α-butylglucoside is collected in the aqueous phase which is decolourised in active carbon. 2.5% (p/v) of active carbon is added into a molar solution of lactate of α-butylglucoside. The whole contents is left to incubate under agitation, for 3 hours at 60° C., then filtered to eliminate the active carbon.

EXAMPLE 2

Preparation of Lactic Ester of α-Butylglucoside

In a flask adaptable to a rotating evaporator, the α-butylglucoside (100 mM) and methyl L-lactate (500 mM) is placed in 20 ml of methyl-2 butanol at 60° C. under vacuum. 100 g/l of Novozym® is added, from the lipase of Candida antarctica immobilised on a solid support (Novo Industri, Denmark). The solution is placed again at 60° C. under vacuum (200 mbars).

The filtrate is collected for purification. The lactate of α-butylglucoside is purified by two successive stages. The Novozyme® is eliminated by filtration. The methyl lactate and methyl-2-butanol-2 are eliminated by evaporation under vacuum (80° C.-10 mbars).

EXAMPLE 3

Preparation of 6-O-Oleylα-Butylglucoside by Enzymatic Esterification

A medium has been made up with 1.2 g of oleic acid and 1 g of α-D-butylglucoside. The mixture is brought to 65° C., fusion temperature of α-butylglucoside. After homogenisation, 1 g of Lipozyme®, from the lipase of Mucor miehei immobilised on a solid support (Novo Industri, Denmark) is added.

After 3 days of incubation, the reaction medium is diluted with 20 ml of diethyl ether, then filtered in order to eliminate the Lipozyme®. After filtration, 50 ml of soda (0.02N) is added, in order to make the residual oleic acid in the form of a sodium salt, as well as the residual α-butylglucoside soluble in the aqueous phase.

The organic phase containing the oleic acid ester is evaporated under vacuum in order to eliminate any trace of residual solvent.

As a variant, Novozyme®, at a concentration of 5% in weight in relation to the substrates, has been substituted for Lipozyme®. Equally an inferior alkyl (methyl or ethyl, for example) oleate can be substituted for oleic acid.

Measures by HPLC have shown that more than 95% of the acid can be converted whatever the enzyme and the acylated compound chosen. However the use of Novozym® as biocatalyst leads to higher conversion with more than 98% of the two substrates which have been converted.

The control of the reaction by Thin Layer Chromatography (TLC) has shown a formation of a single product when the Novozyme® has been used as biocatalyst.

The structure of the products has been determined by Mass Spectrometry (MS) Nuclear Magnetic Resonance (NMR).

After acylation of α-butylglucoside with the oleic acid with Novozym® as a catalyst, the product has been purified.

The results of MS show a molecular ion at m/z=523.3 [M+Na]$^+$, M corresponds exactly to the molecular mass of monooleate of α-butylglucoside. The results of NMR have demonstrated that α-butylglucoside has been grafted exclusively on position 6 of the molecule.

The chemical displacement of the proton at 5.42 ppm confirms the presence of a carbon-carbon unsaturation coming from the oleic part of the molecule 6-O-oleyl α-butylglucoside. The iodine indices from the reaction medium at the beginning (mixture of oleic acid and α-butylglucoside) and at the end (6-O-oleyl α-butylglucoside) of the enzymatic esterification are the same at less than 3% of error (43.7 and 42.7 respectively). That shows that no oxydation of the double link occurred during the process of enzymatic esterification.

EXAMPLE 4

Synthesis of a Mixture of α-Butylglucoside Esters

The acylation of α-butylglucoside is proceeded to by a commercial mixture of linoleic acid (60.5% molar), oleic acid (32.7% molar) and linoleic acid (6.8% molar) in the absence of solvent, at 60° C. under a reduced pressure of 20 mbars, with an initial acid/α-butylglucoside molecular yield of 1, and in the presence of Novozym® to an initial concentration of 5% in weight in comparison to the total weight of the acid reactives and α-butylglucoside.

The water generated by the reaction has been evaporated under established reduced pressure, in order to displace the thermodynamic equilibrium in favour of the synthesis of esters.

The esters produced have been collected by adding a bit of hexane then by eliminating the enzyme by filtration.

The conversion of the initial acids into esters of α-butylglucoside has been almost total (>95%).

As an example, and without it being considered as limiting, the improvement of cutaneous and ocular irritation created by the grafting of a preparation onto α-butylglucoside is described below.

EXAMPLE 5

Comparison of the Cytotoxicity of Lactic Acid and of Lactate of α-Butylglucoside We have quantified and compared in vitro, the cytotoxicity of lactic acid and of lactate of α-butylglucoside on a skin model. This skin model is made up of a matrix of collagen on which rests an epidermis reconstituted from keratinocytes and presenting a similar architecture to that of the human epidermis. The transformation of tetrazolium salt (MTT) in blue crystals of Formozan is proportional to the activity of the dehydrogenase succinate, (a mitochondrial enzyme). As a consequence, the more the epidermis contains living cells, the larger the transformation by the dehydrogenase succinate of the MTT in blue Formozan crystals will be. The quantity of Formozan is measured in the spectrophotometer. The cellular viability, carried out to determine the toxicity of the product, is calculated according to the formula:

% viability=OD produced/OD cellular control×100

The cellular control is carried out without issue. A reference tensioactive SDS (Sodium Dodecyl Sulphate) at 1.5 mg/ml is equally tested as a cytotoxic control.

If the cellular viability is between 70 and 50%, the products are considered as slightly cytotoxic.

If it is lower than 50%, the products are considered as cytotoxic.

Table 2 shows the results of the evaluation.

TABLE n°2

MTT dosage on skin model optical densities obtained at 540 nm and percentage of viability of epidermic cells in comparison to the control

| Trial | Control | SDS at 1–5 mg/ml | Lactic acid at 5% | Lactate of α-butyl glucoside at 5% |
|---|---|---|---|---|
| OD trial 1 | 0.324 | 0.046 | 0.044 | 0.242 |
| OD trial 2 | 0.363 | 0.056 | 0.066 | 0.265 |
| Average | 0.343 | 0.051 | 0.055 | 0.255 |
| % viability in comparison to the control | 100% | 14.8% | 16% | 74.5% |

The lactate of α-butylglucoside, vectorized lactic acid, is less irritant than lactic acid. Lactate of α-butylglucoside at 5% is not cytotoxic.

EXAMPLE 6

Comparison of the Ocular Toxicity of lactic Acid and of Lactate of α-Butylglucoside (Vectorized Lactic Acid)

The BCOP test (bovine corneal opacity and permeability) makes it possible to evaluate the ocular irritation indice in vitro on corneas from abattoir beef carcasses. It measures two parameter of ocular irritation: the opacity and cellular permeability.

The opacity is defined as the difference of light transmission between a treated cornea and a control cornea. The permeability is equal to the optical density (OD) measured in a spectrophotometer at 490 nm.

The irritation score in vitro is established by using the following formula:

Score in vitro=opacity value+1.5 times the value of OD.

The objective values are combined and the scores of ocular irritation in vitro are compared to an irritation scale previously established. In general, the irritant potential is classed in three categories weak (0 to 25), moderate (25.1 to 55) and severe (55.1 and +). The ocular irritation indice in vitro of lactate of α-butylglucoside at 36% is zero although that of lactic acid at 5% and 10% are, respectively from 1.93 and from 41.11.

Our preparation of α-butylglucoside at 36% thus belongs to the category of non-irritant products, whilst lactic acid at 10% belongs to the category of moderately irritant products.

What is claimed is:

1. A method of causing enhanced transcutaneous or transmucous permeation in a patient of an active ingredient in a pharmaceutical, dermatological, cosmetic or food composition, comprising:

applying said composition to skin or mucous membrane of said patient, said composition comprising said active ingredient as a vectorized compound of the formula:

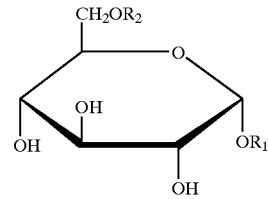

wherein $R_2$ is a —CO—R group in which R is a

radical, with X being an aliphatic chain, and $R_1$ is linear or branched $C_2$–$C_{18}$ alkyl.

* * * * *